United States Patent [19]

Chapman et al.

[11] 4,059,649
[45] Nov. 22, 1977

[54] COOLING OF RECYCLE HYDROCARBON AND/OR ALKYLATE PRODUCT IN ISOPARAFFIN-OLEFIN ALKYLATION

[75] Inventors: Charles C. Chapman; Paul D. Hann, both of Bartlesville, Okla.

[73] Assignee: Phillips Petroleum Company, Bartlesville, Okla.

[21] Appl. No.: 711,185

[22] Filed: Aug. 3, 1976

[51] Int. Cl.$^2$ .............................................. C07C 3/54
[52] U.S. Cl. ............................................... 260/683.48
[58] Field of Search ............... 260/683.4 F, 683.48, 260/683.62, 683.58

[56] References Cited

U.S. PATENT DOCUMENTS

| | | | |
|---|---|---|---|
| 2,334,955 | 11/1943 | Putney | 260/683.48 |
| 2,829,181 | 4/1958 | Stiles et al. | 260/683.48 |
| 2,859,260 | 11/1958 | Stiles | 260/683.48 |
| 2,977,397 | 3/1961 | Putney | 260/683.48 |
| 3,211,536 | 10/1965 | Van Pool | 260/683.48 |
| 3,857,904 | 12/1974 | Chapman | 260/683 |
| 3,925,501 | 12/1975 | Putney, et el. | 260/683 |
| 3,970,720 | 7/1976 | West | 260/683.4 F |

Primary Examiner—George Crasanakis

[57] ABSTRACT

In a process for alkylation of at least one isoparaffin with at least one olefin in the presence of an acid catalyst in which at least a portion of hydrocarbon liquid from the settler is flashed and used as indirect coolant in the alkylation process, the pressure of the liquid withdrawn from the settler is increased prior to flashing. The pressure imparted to the liquid is sufficiently high to allow hydrocarbon vapors containing acid to pass to a fractionator without the use of a compressor.

9 Claims, 2 Drawing Figures

COOLING OF RECYCLE HYDROCARBON AND/OR ALKYLATE PRODUCT IN ISOPARAFFIN-OLEFIN ALKYLATION

BACKGROUND OF THE INVENTION

This invention relates to an improved process of alkylation of at least one isoparaffin with at least one olefin in the presence of an acid catalyst. In particular, it relates to an alkylation process in which at least a portion of the hydrocarbon liquid withdrawn from a settler is flashed to provide indirect cooling for the alkylation process.

Since the temperature at which alkylation of isoparaffin with at least one olefin in the presence of an acid catalyst (such as HF) is inversely proportional to the octane value of the alkylate produced, it is desirable to carry out the alkylation at a minimum attainable temperature. The cooling of the reaction zone can be provided by any suitable means, but it is economically advantageous to utilize the cooling from within the system. One method proposed for cooling of the alkylation zone, disclosed, for example, in U.S. Pat. No. 3,925,501, is by flashing hydrocarbon liquid withdrawn from the settling zone. The flashing provides cooling which reduces the temperature in the reaction zone. The flashed vapor which contains HF therein is transported into a compressor where its pressure is increased to a level sufficient to pass it to a depropanizer. One problem with this process is the cost associated with the use of a compressor. The usually expensive piece of process equipment is made economically unaffordable by the requirement that those parts which come in contact with hydrofluoric acid must be made of materials which are not corroded by vaporized HF. Since materials that are not corroded by acids such as HF are extremely difficult to obtain and their costs are enormous, the compressors made from these are not readily available and must be custom-made. If the material is even slightly corrosive, frequent replacements of parts increase maintenance costs.

The present invention obviates some of the problems encountered in the prior art. Thus, one object of the present invention is to provide an improved alkylation process.

Another object of the invention is to provide an alkylation process which requires a minimum amount of energy.

Still another object of the invention is to provide a process which will reduce the equipment expenses and maintenance expenses.

A still further object of the invention is to provide a process which utilizes commercially available, mass-produced, inexpensive components.

Other objects of the invention will become apparent to those skilled in the art upon studying this disclosure.

SUMMARY OF THE INVENTION

In accordance with one aspect of the invention, in a process for alkylation of at least one isoparaffin with at least one olefin in the presence of an acid catalyst, at least a portion of the acid-containing hydrocarbon effluent liquid from the settling zone is flashed and used as indirect coolant in the alkylation process. The liquid taken off from the settling zone is pressurized to a sufficiently high level to allow the vapor obtained by flashing the liquid to enter a fractionating zone, after it cools a portion of the alkylation system, without the use of a compressor.

In accordance with another aspect of the invention, in a process for alkylation of at least one isoparaffin with at least one olefin in the presence of HF catalyst, a portion of the HF-containing hydrocarbon effluent liquid from the settler is partially vaporized or flashed and used as indirect coolant in the alkylation process. The portion of the liquid which is to be flashed is first pressurized by pump means to a level sufficient to allow the vapor formed upon flashing to enter a fractionating zone after it cools a portion of the alkylation system without the use of a compressor. The amount of liquid that is flashed is the amount that contains the amount of propane equal to the sum of the amount of propane in the feed stream and the amount of propane produced in the alkylation process.

Other aspects of the invention will become apparent upon studying this specification and the appended claims.

DETAILED DESCRIPTION OF THE INVENTION

Figure 1:
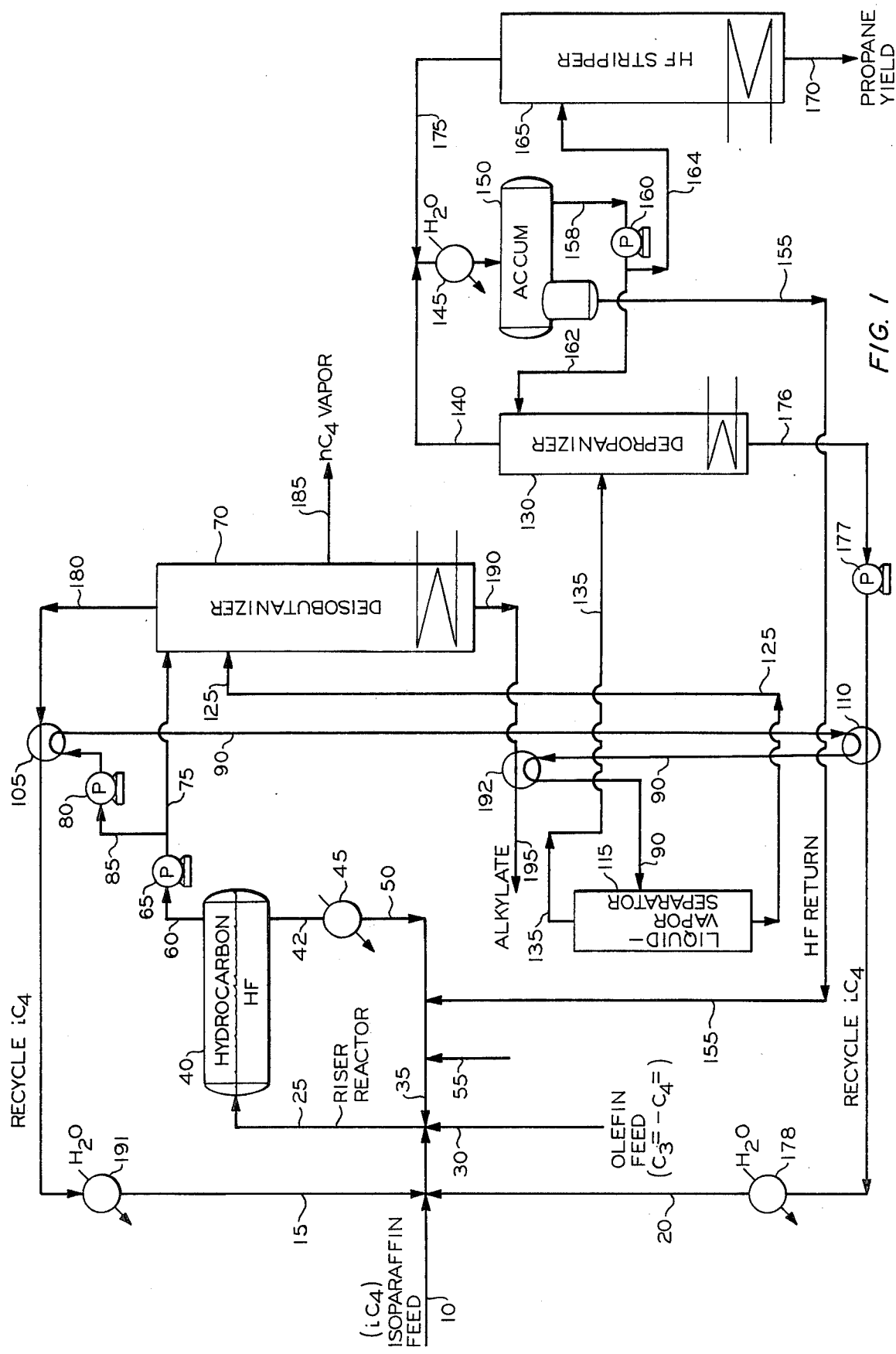
FIG. 1 depicts the schematic of an HF alkylation process in which the present invention is utilized.

In the process of alkylation of an isoparaffin and olefin in the presence of an acid catalyst (such as HF) the reaction temperature is inversely proportional to the octane number of the produced alkylate. It is therefore essential to conduct the alkylation reaction at a minimum permissible temperature. In order to save energy supplied to the system, at least a portion of the cooling can be provided by flashing effluent liquid withdrawn from the settling zone. It has been discovered that if a sufficient pressure is imparted to the liquid, as by pumping, before it is vaporized or flashed, the resulting vapors can be charged to the depropanizer without employing any additional means to promote the transport. The pressure that must be imparted to the liquid prior to vaporizing or flashing varies, depending on the particular system. Usually the minimum pressure is in the range from about 250 psig to about 350 psig (1800–2500 kPa). The upper limit of the pressure is defined only by the structural strength of the equipment. Depending upon liquid composition, when the pressure is suddenly reduced to about 250–300 psig (1800–2150 kPa), rapid evaporation of a portion of the liquid ensues. The transition from liquid to vaporous state utilizes energy present in the system and thereby provides a cooling effect. The cooling can be utilized to lower the temperature in the alkylation system. The heat can be withdrawn from the desired portion of the alkylation system by indirect heat exchange with the reaction mass, one of the streams flowing to the reaction zone, the alkylate stream prior to its storage, or any of these. Under usual operating conditions, it is preferable to utilize the cooling produced by flashing a portion of the pressurized hydrocarbon liquid effluent for cooling the recycle isoparaffin stream or streams. The reason for the preference is that the recycle isoparaffin stream from fractionation is normally at a higher temperature, the temperature difference being about 50° F (28° C) to about 250° F (139° C), than that of the other streams entering the reaction zone or the reaction mass, thus making heat exchange more efficient. Recycle isobutane also is the largest volume hydrocarbon stream.

Alternatively, at least some of the cooling produced by flashing of the compressed liquid can be used for cooling the alkylate stream taken off as product from the fractionator. Usually that stream is at a temperature from about 300° F (149° C) to about 400° F (204° C). Since in normal operation the alkylate is stored at ambient temperature and pressure equal or only slightly above atmospheric, to prevent rapid evaporation of the hot alkylate stream the stream is cooled prior to storing to a temperature of about 90° F (32° C). The cooling of the alkylate can at least partially be accomplished by heat exchange with the pressurized hydrocarbon effluent. The pressurized hydrocarbon liquid used in indirect cooling of isoparaffin and of alkylate is at the same time heated to the proper temperature (while already at its proper pressure) for being charged to fractionation from a final vapor liquid separation zone.

In the process, the isoparaffin to olefin mole ratio can vary considerably, but it generally is in the range from about 2:1 up to about 25:1, usually from about 4:1 to about 15:1. The total hydrocarbon to HF catalyst volume ratio can vary considerably depending on the specific system, but the usual range is from about 1/10 to about 10/1. The HF alkylation reaction can be carried out in a wide temperature range, usually in the range from about 0° F ($-18°$ C) to about 150° F (66° C), and at a pressure sufficient to maintain liquid phase conditions. The lower the reaction temperature, the higher the octane number of the alkylate. Since it is less expensive to use cooling water, the normal reaction zone temperature is about 90° C (32° C).

Any isoparaffin, alone or in admixture with another isoparaffin, is suitable for use with the present invention including isobutane, isopentane, and isohexanes. Among olefins that can be used are propylene, butylenes, amylenes, and many others, alone or in admixture with other olefins.

The invention is particularly suitable for the process of alkylation of isobutane with propylene and butylenes. Any portion of the hydrocarbon liquid effluent from the settler can be pumped to high pressure, used as heat exchange (coolant) and partially vaporized; however, in some embodiments, it is preferred to vaporize only that portion of the hydrocarbon liquid effluent which contains the amount of propane equal to the sum of the amount fed into the reaction zone and the amount produced by the reaction so this propane can be removed from the system.

Figure 2:
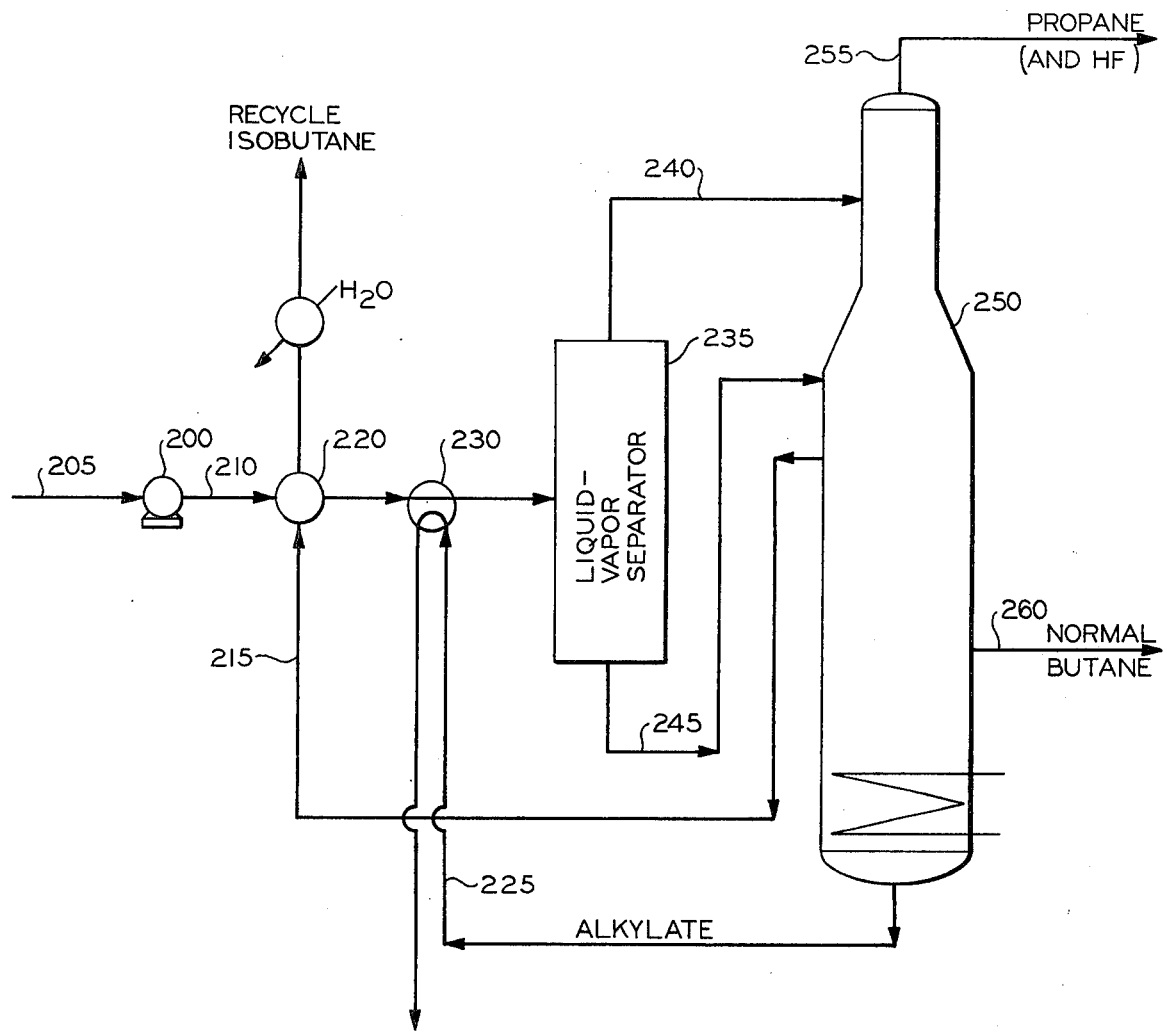
FIG. 2 depicts the schematic of a portion of another HF alkylation process in which the present invention is utilized.

The invention can be further explained by referring to the specific embodiments depicted in FIGS. 1 and 2.

Referring now to FIG. 1, the isoparaffin feed passed through 10 combines with isoparaffin recycle streams 15 and 20. The combined isoparaffin streams 10, 15, and 20 are introduced into the riser reactor 25 together with olefin feed passed by 30 and hydrofluoric acid passed by 35. The conditions in the riser reactor, including temperature and pressure, are maintained at such levels as to achieve liquid phase alkylation of the isoparaffin with the olefin in the presence of HF. From the riser reactor 25 the reaction mass is passed to a phase separator 40 which is also maintained at conditions which retain the reaction mass in the liquid state. In separator 40 the alkylation reactor effluent is allowed to form an upper phase containing primarily hydrocarbons and a lower phase containing mainly hydrofluoric acid. The lower phase is passed via 42 from the phase separator 40 to a cooler 45 and therefrom through 50 and 35 to the riser reactor 25. Make-up hydrofluoric acid can be supplied to the system through 55.

The upper phase from the phase separator 40 is passed by 60 to a transport pump 65 which causes one portion of the hydrocarbon stream to flow to deisobutanizer 70 via 75 and another portion of that stream via 85 to a pump 80 where the pressure on the liquid is increased, leaving pump 80 via 90. The pump 80 causes the pressure of the liquid to rise to a sufficiently high level to allow vapors obtained by heating and flashing a portion of hydrocarbon stream 90 to enter the depropanizer 130 without any HF-containing vapor compression. The pressured liquid flashed in line 90 is utilized in indirect cooling of recycle isobutane streams 15 and 20 using heat exchangers 105 and 110, respectively, and cooling of alkylate 190 in indirect exchanger 192. The heated and partially vaporized stream 90 is then passed to a liquid-vapor separator 115. The liquid phase separated in the separator 115 which comprises alkylate and isobutane is passed to the top section of deisobutanizer 70 via 125. The vapor phase comprising propane and HF is introduced into depropanizer 130 via 135. The conditions in the depropanizer are such as to separate the materials introduced therein into a depropanizer overhead and depropanizer bottoms. The depropanizer overhead is taken off as a depropanizer overhead stream 140 which is condensed in an exchanger 145 and passed therefrom to an accumulator 150. In the accumulator cooled overhead stream 140 is allowed to separate into a liquid HF phase, which is withdrawn by 155 and combined with 35, and a liquid hydrocarbon phase, carried by 158, one portion of which is pumped by a depropanizer pump 160 via 162 into the top of, as reflux for, depropanizer 130 and another portion of which is passed by the same pump via 164 to the top of HF stripper 165. Therein conditions are such as to separate propane from HF. Propane liquid is removed from the bottom of HF stripper 165 via 170; the stripper overhead vapor comprising HF and propane is passed via 175 to condenser 145.

The depropanizer bottoms liquid, composed essentially of isobutane, is withdrawn from depropanizer 130 via 176 and passed by recycle pump 177 into heat exchanger 110. Therein the recycle stream is cooled by indirect heat exchange with the fluid in 90. The cooled isobutane stream is then directed to recycle stream cooler 178 in which the stream is further cooled and then passed via 20 to the reaction zone.

The materials introduced into deisobutanizer 70 are separated as the result of conditions maintained therein into a deisobutanizer overhead vapor comprising isobutane and propane, an intermediate cut comprising mainly normal butane, and deisobutanizer bottoms comprising mainly alkylate product. These components are withdrawn from deisobutanizer 70 by 180, 185, and 190, respectively. The recycle isoparaffin stream 180 is cooled in heat exchanger 105 and further cooled by a recycle cooler 191. The other two streams, 185 and 190, are withdrawn from the deisobutanizer as products. Alkylate stream 190, as described above, is cooled in alkylate heat exchanger 192 and therefrom passed by 195 to additional coolers and storage (not shown).

FIG. 2 depicts the schematic of a portion of the alkylation process utilizing the same reaction as shown in FIG. 1. Starting at the point of the alkylation process where liquid hydrocarbon effluent exits from the phase separator (not shown), the entire hydrocarbon effluent phase is passed to a hydrocarbon effluent pump 200 via 205. The pressure of the liquid is increased to a level sufficient to permit passing of vapor obtained by subsequent heating of the hydrocarbon effluent stream into a fractionator without any means of HF-containing vapor compression. In this particular system, the pressure of the liquid is increased to about 230 psig (1680 kPa).

The pressured liquid in line 210 is used for indirectly cooling a recycle isobutane stream 215 by means of a heat exchanger 220 and the alkylate stream 225 using heat exchanger 230. From line 210 after heat exchanger 230, the partially vaporized hydrocarbon stream 210 is introduced into a liquid-vapor separator 235. Vapor stream 240 and liquid stream 245 are removed from separator 235. Vapor stream 240 is introduced near the top to a fractionator 250; liquid stream 245 is fed to the same fractionator near its midsection. The temperature and pressure in the fractionator are such as to separate the materials introduced thereto into an overhead comprising mainly propane and some HF, intermediate cuts, one comprising isobutane and the other comprising mainly normal butane, and bottoms comprising essentially alkylate. These fractions having temperatures of 150° F (66° C), 190° F (88° C), 200° F (93° C), and 420° F (216° C) are withdrawn from fractionator 250, which is maintained at about 200 psig (1480 kPa), via 255, 215, 260, and 225, respectively. The propane-HF stream 255 can be further passed to an HF stripper (not shown) to recover HF and propane contained therein. HF can then be recycled to the reaction zone (not shown) and propane can be recovered as product.

The following example merely illustrates the practice of the invention and is not intended to limit in any manner the scope of the invention.

EXAMPLE

Using the process of the invention shown in FIG. 1, the following flow rates and the following operating conditions in specific components of the systems were calculated:

| Typical Flow Rates | |
|---|---|
| Fresh Isobutane (10), B/D | |
| 95% iC$_4$ by volume | 4,800 |
| Olefin Feed (30), B/D | |
| 54% C$_3$=, C$_4$= olefins by volume | 9,200 |
| Recycle Total Isobutane (15 and 20), B/D | |
| 86% iC$_4$ by volume | 78,000 |
| To Deisobutanizer (70) via (75), B/D | 50,000 |
| Pressure, psig | 150 |
| kPa | 1,130 |
| To Exchanger (105) via (85), B/D | 41,400 |
| Vapor (135) to DeC$_3$ (130), B/D | 20,700 |
| nC$_4$ Yield (185), B/D | 800 |
| Propane Yield (170), B/D | 1,500 |

| OPERATING CONDITIONS IN SPECIFIC COMPONENTS | |
|---|---|
| Reactor Riser (25): | |
| Temperature, ° F (inlet) | 85 |
| Pressure, psig | 105 |
| Pressure, kPa | 825 |
| HF/Total Hydrocarbon Vol. Ratio | 4 |
| iC$_4$/Olefin Mol Ratio, About | 14 |
| Separator (40): | |
| Temperature, ° F | 100 |
| Pressure, psig | 90 |
| Pressure, kPa | 720 |
| Deisobutanizer (70): | |
| Top Zone: | |
| Temperature, ° F | 150 |
| Pressure, psig | 120 |
| Pressure, kPa | 930 |
| Bottom Zone: | |
| Temperature, ° F | 350 |
| Pressure, psig | 125 |
| Pressure, kPa | 960 |
| Liquid-Vapor Separator (115): | |
| Temperature, ° F | 220 |
| Pressure, psig | 285 |
| Pressure, kPa | 2070 |
| Depropanizer (130): | |
| Top Zone: | |
| Temperature, ° F | 125 |
| Pressure, psig | 260 |
| Pressure, kPa | 1895 |
| Bottom Zone: | |
| Temperature, ° F | 245 |
| Pressure, psig | 265 |
| Pressure, kPa | 1930 |
| HF Stripper (165): | |
| Top Zone: | |
| Temperature, ° F | 127 |
| Pressure, psig | 295 |
| Pressure, kPa | 2135 |
| Bottom Zone: | |
| Temperature, ° F | 145 |
| Pressure, psig | 300 |
| Pressure, kPa | 2170 |
| Material in Conduit (85): | |
| Outlet at Pump (80): | |
| Temperature, ° F | 100 |
| Pressure, psig | 325 |
| Pressure, kPa | 2340 |
| Inlet to Separator (115): | |
| Temperature, ° F | 220 |
| Pressure, psig | 285 |
| Pressure, kPa | 2070 |

Using the process shown in FIG. 1 and flow rates and operating conditions specified in this example, estimated heat savings over the conventional process are in the range from about 20-25 million Btu per hour. The savings result from:

1. Utilization of heating, vaporizing, or flashing liquid hydrocarbon effluent for cooling the reaction zone system.
2. Smaller size of depropanizer 130 as the result of priorly separating about 45 percent of the feed 135 (normally introduced to the depropanizer) in the separator 115.
3. Smaller size of the deisobutanizer 70 as the result of recycling stream 176, containing only about one percent of alkylate, directly to the reaction zone instead of introducing it to the deisobutanizer.

All kPa pressures are reported as absolute pressures.

We claim:
1. An alkylation process which comprises:
   a. reacting in a reaction zone at least one isoparaffin with at least one olefin in the presence of a sufficient amount of an acid catalyst at liquid phase reaction conditions for a period of time sufficient to form alkylate;
   b. separating the reaction effluent to form a liquid acid phase and a liquid hydrocarbon phase;
   c. maintaining conditions in the separation zone of step (b) to retain the hydrocarbon phase in the liquid state;
   d. pressurizing at least a portion of the liquid hydrocarbon phase from said separation zone to produce a pressurized liquid hydrocarbon stream;
   e. vaporizing a portion of the pressurized liquid hydrocarbon stream by reducing the pressure on said pressurized liquid hydrocarbon stream;

f. maintaining a pressure on said vaporized hydrocarbons sufficient to permit the entry of vaporous hydrocarbons into a fractionating zone;

g. subjecting hydrocarbons entering said fractionating zone to fractionating conditions and withdrawing a fractionator overhead comprising a mixture of paraffin and said acid catalyst, an intermediate cut comprising unreacted isoparraffin stream and a bottoms streams comprising essentially alkylate;

h. recycling said isoparaffin stream to the reaction zone; and i. utilizing said pressurized liquid hydrocarbon stream produced in step (e) to cool at least one of said bottoms stream, and said unreacted isoparaffin stream.

2. A process as claimed in claim 1 wherein said isoparaffin is isobutane, said olefin comprises at least one of propylene, butylene, and amylene, said acid catalyst is hydrofluoric acid, the reaction temperature is in the range from about 0° F (−18° C) to about 150° F (66° C), the isoparaffin to olefin mole ratio range is from about 2:1 to about 25:1, the volume ratio of hydrofluoric acid to the combined volume of olefin and isoparaffin is from about 1/10 to about 10/1, and the pressure imparted in step (d) is in the range from about 250 to about 350 psig (1800–2500 kPa).

3. A process as claimed in claim 2 wherein said pressurized liquid hydrocarbon stream produced in step (e) is utilized to cool said isoparaffin stream.

4. A process as claimed in claim 2 wherein only the portion of the pressurized hydrocarbon stream that contains propane equal to the sum of the amount of propane introduced as impurities into the reaction zone and the amount of propane produced in the reaction zone is vaporized in step (e).

5. An alkylation process which comprises:
   a. reacting in a reaction zone at least one isoparaffin with at least one olefin in the presence of a sufficient amount of acid catalyst at liquid phase conditions for a period of time sufficient to form alkylate;
   b. separating the reaction effluent to form a liquid acid phase and a liquid hydrocarbon phase;
   c. maintaining conditions in the separation zone of step (b) to retain the hydrocarbon phase in the liquid state;
   d. pressurizing a first portion of the liquid hydrocarbon phase from said separation zone to produce a pressurized liquid hydrocarbon stream;
   e. vaporizing a portion of the pressurized liquid hydrocarbon stream by reducing the pressure on said pressurized liquid hydrocarbon stream;
   f. separating the pressurized liquid hydrocarbon of step (e) in a liquid-vapor separation zone into a hydrocarbon liquid stream and a hydrocarbon vapor stream;
   b. maintaining a pressure sufficient on said hydrocarbon vapor stream of step (f) sufficient to permit entry of said vapor stream into a depropanizing zone;
   h. passing the hydrocarbon liquid stream of step (f) into an isoparaffin fractionation zone;
   i. introducing a second portion of the liquid hydrocarbon phase from said separation zone into said isoparaffin fractionation zone;
   j. separating the liquid hydrocarbon steams of step (h) and step (i) in said isoparaffin fractionation zone and withdrawing from said zone an overhead hydrocarbon comprising mainly isoparaffin and a bottoms hydrocarbon product comprising essentially alkylate;
   k. recycling said overhead hydrocarbon to said reaction zone, and
   l. utilizing said pressurized liquid hydrocarbon stream produced in step (e) to cool at least one of said overhead hydrocarbon and said bottoms hydrocarbon product.

6. A process as claimed in claim 5 wherein said pressurized liquid hydrocarbon stream produced in step (e) is utilized to cool said isoparaffin stream.

7. A process as claimed in claim 8 wherein only the portion of the pressurized hydrocarbon stream that contains propane equal to the sum of the amount of propane introduced as impurities into the reaction zone and the amount of propane produced in the reaction zone is vaporized in step (e).

8. A process as claimed in claim 6 further comprising:
   m. withdrawing from said depropanizing zone a depropanizer overhead containing mainly propane and a small amount of hydrofluoric acid and a depropanizer bottoms containing essentially isobutane;
   n. recycling the depropanizer bottoms stream of step (m) to the reaction zone;
   o. separating by phase separation the depropanizer overhead stream of step (m) into a hydrofluoric acid stream and a propane stream;
   p. passing the hydrofluoric acid stream to the reaction zone and the propane stream to a stripping zone;
   q. stripping said propane stream in said stripping zone withdraw therefrom stripper overhead comprising mainly hydrofluoric acid and stripper bottoms comprising essentially propane; and
   r. recycling the stripper overhead stream to the phase separation of step (o).

9. In the process of alkylating at least one isoparaffinic hydrocarbon with at least one olefinic hydrocarbon in the presence of HF acid catalyst in a reaction zone and wherein the reaction mixture is separated into a liquid hydrocarbon phase and an HF acid catalyst phase and wherein the separated liquid hydrocarbon phase is subjected to fractional separation of propane, HF acid, and butanes from alkylate product, the improvement comprising:
   a. raising the pressure of at least a portion of the separated liquid hydrocarbon phase;
   b. heat exchanging indirectly said portion of said pressurized liquid hydrocarbon phase with recycle hydrocarbon streams and alkylate product stream;
   c. reducing pressure on said pressurized liquid hydrocarbon phase of step (b) while retaining pressure sufficient to provide hydrocarbon vapor feed for depropanizing fractionation and liquid feed for debutanizing fractionation;
   d. feeding hydrocarbon vapor to a depropanizing fractionation; and
   e. feeding liquid to a debutanizing fractionation.

* * * * *